United States Patent [19]

Rhandhawa

[11] Patent Number: 4,981,756
[45] Date of Patent: Jan. 1, 1991

[54] METHOD FOR COATED SURGICAL INSTRUMENTS AND TOOLS

[75] Inventor: Harbhajan S. Rhandhawa, Boulder, Colo.

[73] Assignee: Vac-Tec Systems, Inc., Boulder, Colo.

[21] Appl. No.: 553,360

[22] Filed: Jul. 13, 1990

Related U.S. Application Data

[63] Continuation of Ser. No. 326,322, Mar. 21, 1989, abandoned.

[51] Int. Cl.$^5$ .......................... B32B 15/04; B05D 3/02
[52] U.S. Cl. ..................................... 428/336; 427/327; 427/328; 427/376.8; 428/457; 428/698; 428/699
[58] Field of Search ................ 433/165; 428/457, 698, 428/699, 336; 427/376.8, 327, 328

[56] References Cited

U.S. PATENT DOCUMENTS

| | | | |
|---|---|---|---|
| 4,104,417 | 8/1978 | Sara | 428/457 X |
| 4,662,288 | 5/1987 | Hastings et al. | 428/359 X |
| 4,681,541 | 7/1987 | Snapper | 433/165 |
| 4,682,987 | 7/1987 | Bradly et al. | 457/376.3 X |

FOREIGN PATENT DOCUMENTS

| | | |
|---|---|---|
| 59-76872 | 5/1984 | Japan . |
| 621476 | 2/1981 | Switzerland . |

OTHER PUBLICATIONS

Copy of brochure published by Balzers Tool Coating, Inc., published 1–1987, 2 pages.

*Primary Examiner*—Thomas J. Herbert
*Attorney, Agent, or Firm*—Beaton & Swanson

[57] ABSTRACT

A process for producing corrosion resistant and wear resistant medical tools and instruments by coating high strength low-carbon martensitic stainless steels with a thin, hard layer of refractory metal compound, preferably via cathodic arc plasma deposition technology. The invention also covers the coated medical tools produced via such process.

19 Claims, No Drawings

METHOD FOR COATED SURGICAL INSTRUMENTS AND TOOLS

This is a continuation of co-pending application Ser. No. 326,322, filed on Mar. 21, 1989, now abandoned.

FIELD OF THE INVENTION

The present invention relates to coated instruments and tools for use in surgery and other medical applications. The coating consists of a hard wear resistant and corrosion resistant material. One preferred coating is zirconium nitride that has been applied by the cathodic arc plasma deposition process.

BACKGROUND OF THE INVENTION

Surgical tools and instruments must possess certain characteristics in order to qualify for medical use. These characteristics include hardness, nick-free cutting edges and corrosion free surfaces. Such tools are conventionally manufactured using 400 series stainless steels. The 400 series stainless steels, or martensitic stainless steels, are low carbon stainless steels that are easy to sterilize and have high mechanical strength. However, such steels are relatively susceptible to corrosion and extreme care must be taken with their storage. The cost of medical tools and instruments made of these materials is extremely high.

The proper grain structure in the cutting edges of medical tools such as scalpels, scissors, elevators, curettes, vice grips, etc. is critical. The appropriate grain structure allows the instrument to properly cut bone surfaces during surgery and create an area where bone regrowth can find a good "grip" for the new bone fusion. Any nicks appearing on the cutting edge may be transferred to the bone being cut during surgery and may lead to trauma that will slow down post-surgery healing.

Unfortunately, the various requisite and desirable characteristics for medical tools and instruments are not currently available in a single type of tool or instrument. Although the strength and grain structure requirements are met by the current devices made of 400 series stainless steel, the costly tools and instruments have a very short lifetime due to their tendency to rapid corrosion.

The corrosion resistance of any material used for manufacturing medical tools and instruments is always quickly put to the test. For both historical and sanitary reasons, all such instruments and tools are "sterilized" under severe conditions following each use. Typically, medical tools and instruments are soaked in a concentrated solution of caustic, rinsed and then steam/gas sterilized in an autoclave between each usage. Both the soaking and autoclaving processes dramatically promote the oxidation or corrosion of metal surfaces. The costly medical tools and instruments that are currently used in surgery and medical applications are often made useless due to corrosion after only 5 to 10 uses.

This invention describes a method for applying a thin hard coating on surgical tools and instruments. The resulting tools have superior edge retention, superior corrosion resistance and long tool life.

Japanese Patent No. 59-76872 of Okubo describes a method for manufacturing metal medical and dental instruments such as razor blades, scalpels, scissors and forceps. A coating of nickel or nickel alloy, chromium or chromium alloy, or a coating of gold alloy is applied to the surface by wet plating methods. Next, a hard coating such as a nickel phosphorous alloy is applied to the surface of the instruments. The last step of the invention is the application of a hard film of titanium nitride by an ion plating method.

One of the objectives of the inventors of the Japanese patent was to produce less costly medical tools and instruments. In so doing, their invention contemplates the use of less expensive, relatively low quality substrates of iron or iron alloys. The complicated procedure of applying several coating layers is necessary due to this choice of substrate material. The direct application of titanium nitride on such substrates would result in poor adhesion and corrosion resistance due to galvanic cell formation between the iron of the substrate and the nitride film, making any such tools highly undesirable for medical purposes. In addition, any process calling for several steps utilizing wet plating methods is environmentally suspect.

Swiss Patent No. 5297/78 of Hintermann et al. describes cutting instruments specifically designed for use by Ophthalmologists. The instruments are made of steel that has been coated with a titanium carbide, nitride or carbonitride film. In the completed article, the cutting edge remains uncoated. The patent suggests that deposition of the coating may be accomplished by vacuum evaporation, ion plating or chemical deposition processes.

The chemical deposition process is accomplished by a gas phase chemical reaction generally occurring at extremely high temperatures such as approximately 1000° C. At such elevated temperatures, there would be a significant reduction in the mechanical strength and wear properties of the steel substrate. Chemical deposition processes are, therefore, unsuitable for coating tools and instruments for medical or surgical purposes.

The titanium nitride or titanium carbide films obtained by vacuum evaporation or conventional ion plating techniques, as suggested in the Swiss patent, generally have columnar structure. Coatings having such columnar structure generally must be at least 3 microns thick, will contain voids, and will be a relatively low density surface. This results in relatively poor corrosion protection and wear resistance. Film thicknesses over 3 microns also contribute to poor film adherence due to the high density of compressive stresses in these coatings.

In order for coated instruments to be suitable for surgery, the coatings should have excellent corrosion resistance, wear resistance and good adhesion to bare substrates. This can be achieved by a suitable selection of coatings and coating processes. One superior coating process is the cathodic arc plasma deposition ("CAPD") method.

CAPD has unique features relative to other ion plating techniques. Among these are the ability to generate a high degree of target molecule ionization and higher ion energies. These features lead to the creation of high density coatings with superior bonding to substrate characteristics. High density coatings have relatively fewer voids, and can be applied in much thinner layers while still assuring complete surface coverage.

A suitable film with higher hardness and wear properties than titanium nitride/carbide would also be very desirable. One such coating is zirconium nitride, which has higher hardness than titanium nitride and also possesses a lower co-efficient of friction. Both of these characteristics would suggest that zirconium nitride would be a better candidate material for medical tools and instruments than other metal compounds currently suggested in the literature.

SUMMARY OF INVENTION

The present invention discloses a method for coating medical instruments and tools for surgical and other uses. This invention describes an improved medical tool that is produced by coating stainless steel substrates with zirconium nitride or other refractory metal compounds by the CAPD process or other coating processes capable of placing a high density thin coating on substrates.

The medical instruments and tools of this invention are prepared by coating the substrate surface with a hard coating such as zirconium nitride. Applying such a coating reduces the need for frequent resharpening and, most importantly, greatly reduces the tendency of the instruments to rapidly corrode. Furthermore, the invention allows these instruments to be manufactured with a clean appearance and a variety of color coatings.

The medical tools and instruments of the present invention are especially useful for orthopedic surgery and have significantly enhanced chemical stability/corrosion resistance against caustic soak and steam/gas sterilization. The description and examples provided below are presented in order to help clarify and describe the invention, but are in no way intended to limit the scope of the invention as set forth in the following claims.

DESCRIPTION OF THE PREFERRED EMBODIMENT

This invention relates to improved medical tools and instruments. In particular, this invention relates to surgical tools and instruments for orthopedic procedures. Also disclosed is a method for producing such improved devices. The basic invention relates to medical tools and instruments coated with a thin, hard, wear resistant and corrosion resistant metal compound. The metal of the metal compound will typically be one of the refractory metals. Some of the refractory metals are titanium, hafnium, zirconium, tungsten and molybdenum. Examples of metal compounds particularly suited for use with this invention are: titanium nitride, titanium carbide, titanium carbonitride, zirconium nitride, zirconium carbide, zirconium carbonitride, hafnium nitride, hafnium carbonitride, and hafnium carbide. The preferred metal compounds are zirconium based, and the most preferred coating is zirconium nitride.

The medical tools and instruments include, but should not be limited to, scalpels, scissors, elevators, curettes and vice grips. The uncoated tools and instruments are to be made of a high strength corrosion resistant metal, preferably stainless steel and most preferably 400 series or martensitic stainless steel. Utilizing these grades of substrate tools or instruments promotes the corrosion resistance of the ultimate product, enhances the adhesion of the coating surface to the substrate, and allows for the application of a very thin coating layer.

Such metal compounds may be applied by various coating techniques. Examples of such coating techniques are: vacuum evaporation processes, chemical vapor deposition, electroplating, magnetron sputtering, ion plating, thermal or plasma spray techniques and cathodic arc plasma deposition ("CAPD").

In a preferred embodiment of the invention, the hard coated surface is applied by CAPD technology. CAPD technology is a form of ion plating that may be adapted to provide large area arc sources that assure exceptional film uniformity over small, large and complex substrates, and also provide shorter cycle times and high throughout. In the CAPD process, target material is evaporated and ionized by the action of vacuum arcs. The target source material is the cathode in the arc circuit. The basic components of a CAPD system consist of a vacuum chamber, a cathode and an arc power supply, means for igniting an arc on the cathode surface, an anode, a substrate and a substrate bias power supply. Arcs are sustained by voltages typically in the range of 15–50V, depending on the target cathodic material employed. Typical arc currents are in the range of 30–400A. Arcing is initiated by the application of a high voltage pulse to an electrode placed near the cathode (gas discharge ignition) and/or by mechanical ignition. The evaporation occurs as a result of cathodic arc spots which move randomly on the surface of the cathode at speeds typically on the order of $10^2$ m/s. The arc spot motion can also be controlled with the help of appropriate confinement boundaries and/or magnetic fields. The arc spots are sustained by the material plasma generated with the arc.

The basic CAPD process has evolved over the past twenty years. U.S. Pat. Nos. 3,625,848 and 3,836,451 of Snaper, assigned to Vac-Tec Systems, Inc., provide the origins of the basic process. U.S. Pat. No. 4,430,184 of Mularie and U.S. Pat. No. 4,724,058 of Morrison, Jr. (also both assigned to Vac-Tec Systems, Inc.) teach improvements to the CAPD process. A summary of the CAPD art is provided in "Cathodic Arc Deposition Technology" by H. Randhawa, 167 *Thin Solid Films*, pp. 175–85 (1988). These references are each incorporated herein by this reference.

The disclosures listed above describing the use of hard metal compound coatings were limited to coatings of at least 3 microns thick. Utilizing classical ion plating techniques, it is generally impossible to conformally coat any surface without applying a coating that is generally about 3 microns thick. Utilizing CAPD it is possible to apply layers of from 1–10 microns thick of a metal compound. The medical tools of the present invention are preferably coated with a high density layer of less than 3 microns of a metal compound.

In the preferred embodiment of the invention, medical tools or instruments of high strength martensitic stainless steel are first subjected to a chemical cleaning process to remove surface oils and grime. The examples below describe this process in more detail.

Utilizing CAPD technology, the cleaned tool or instrument to be coated according to this invention is placed within a CAPD apparatus for application of a hard coated metal compound surface. The pressure in the CAPD apparatus is typically reduced to $1 \times 10^{-5}$ Torr in order to remove most of the air and moisture from the system. Nitrogen is then introduced into the apparatus, raising the pressure to approximately $1 \times 10^{-3}$ Torr. The CAPD process consists of a cleaning cycle and a deposition cycle. Optionally, the substrate to be coated is preheated prior to or during the cleaning cycle. The "cleaning" cycle involves two stages. In the first stage, the tool or instrument is bombarded with ions of the system gas which is typically argon. In the second stage of the cleaning process, the substrate is bombarded with ions of the metal target. The deposition cycle occurs when additional nitrogen has been introduced into the CAPD apparatus to obtain an operating pressure between 4 and $20 \times 10^{-3}$ Torr.

The medical tool or instrument produced according to this invention has a thin, hard, wear resistant and corrosion resistant surface. By varying the composition of the process gasses (eg. nitrogen and argon when zirconium nitride is being coated onto the tool or instrument) it is possible to create distinctive and reproduceable color variations. The ability to apply different colors to different medical tools and instruments is a valuable means of differentiating between similar but distinctly different devices. It is also possible to adjust the color in order to help visualize corrosion appearing on the surface of the tool. For example, the appearance of corrosion is easily identified when a zirconium nitride coating has been applied, but hard to distinguish when the surface coating is titanium nitride.

Employing the process for producing wear resistant and corrosion resistant medical tools and instruments as described herein, the tools and instruments produced will generally high an attractive golden-toned finish. If the base tool or instrument has a glossy finish, the final product will also be glossy.

The medical tools and instruments produced have numerous advantages over existing tools and instruments. Because of the hard surface provided, the tools and instruments can be repeatedly used without resharpening any sharp or cutting edges. The coating also provides dramatically improved resistance to corrosion, even when subjected to repeated cycles of use, caustic soak and steam/gas sterilization.

By utilizing the CAPD technique to apply the metal compound coating, it is possible to apply a high density coating. As opposed to those coating techniques which generally have a columnar formation, it is possible to apply coatings with CAPD processes that is conformal and effective in corrosion resistance when only 1 micron thick. Examples

EXAMPLE 1:

Orthopedic surgical tools of 400 series stainless steels were chemically cleaned prior to coating. The chemical cleaning process involved vapor degreasing in an organic solvent, alkaline ultrasonic etch, water rinse and freon dry. The parts were then loaded in a vacuum system. The system was evacuated using mechanical pump and cold trap diffusion pump combinations to reduce the pressure to about $1 \times 10^{-5}$ Torr. The system was then back filled with argon gas to a pressure of 20-25 mTorr. A high voltage of approximately 1 KV was applied to the tools, thereby establishing a glow discharge ion bombardment to further clean the tools inside the vacuum system. The parts were then subjected to zirconium ion bombardment by activating the arc source and reducing the voltage on the tools to 600 V, in the presence of nitrogen gas at 1 mTorr. Next, the nitrogen gas pressure was increased to 10 mTorr and the bias on the tools reduced into the range of 100-300 Volts to commence the coating of zirconium nitride. The coating thickness was adjusted in the range of 2-3.0 microns. The microhardness was found to be in the range of 2600-3000 Kg/mm$^2$.

EXAMPLE II:

Orthopedic surgical tools such as curettes, elevators used to separate tissue from the bone or elevate the bone and vice grips coated according to Example I with 2.5 microns zirconoum nitride films were used in performing actual surgeries. In between surgeries the tools were stored in clorox and were sterilized using steam/gas treatments. The zirconium nitride coated parts showed very little wear or corrosion after 100 surgeries.

EXAMPLE III:

The tools described in Example 2 that were used in actual surgery were coated with 2.5 microns zirconoum nitride films. Wear life data was generated over a period of 90 days and compared with data obtained for uncoated medical tools and instruments. The usable life time of the zirconium nitride coated tools was found to have increased 5-7 times over the uncoated tools subjected to the same conditions.

I claim:

1. A corrosion resistant, coated medical tool consisting of:
    (a) a high strength, solid stainless steel tool; and
    (b) a thin, high-density coating on the surface of said tool of a zirconium-based or hafnium-based metal compound.
2. The medical tool defined in claim 1 in which said stainless steel tool is composed of a low-carbon, martensitic stainless steel.
3. The medical tool defined in claim 1 in which said coating is 1-10 microns thick.
4. The medical tool defined in claim 1 in which said coating is less than 3 microns thick.
5. The medical tool defined in claim 1 in which said metal compound is selected from the group consisting of zirconium nitride, zirconium carbide, zirconium carbonitride, hafnium nitride, hafnium carbide and hafnium carbonitride.
6. The medical tool defined in claim 1 in which said metal compound is applied to cathodic arc plasma deposition.
7. The medical tool defined in claim 1 in which said metal compound is applied by magnetron sputtering.
8. The medical tool defined in claim 1 in which said metal compound is color differentiated.
9. A corrosion resistant, coated medical tool comprising:
    (a) a high strength, low-carbon martensitic stainless steel tool; and
    (b) a high density coating of less than 3 microns composed of zirconium nitride, said coating applied by cathodic arc plasma deposition.
10. A corrosion resistant, coated medical tool consisting of:
    (a) a high strength, solid stainless steel tool; and
    (b) a thin coating on the surface of said tool of zirconium nitride.
11. A process for coating metal medical tools consisting of:
    cleaning said tool prior to coating; and
    applying onto the surface of said tool a coat of a thin high density layer of a zirconium-based or hafnium-based metal compound.
12. A process as in claim 11 in which said tool is composed of low carbon martensitic stainless steel.
13. A process as in claim 11 in which said coat is between 1 and 10 microns thick.
14. A process as in claim 11 in which said coat is less than 3 microns thick.
15. A process as in claim 11 in which said metal compound is selected from the group consisting of zirconium nitride, zirconium carbide, zirconium carbonitride, hafnium nitride, hafnium carbide and hafnium carbonitride.

16. A process as in claim 11 in which said metal compound is zirconium nitride.

17. A process as in claim 11 wherein said cleaning is comprised of ambient pressure cleaning and vacuum ion bombardment cleaning.

18. A process as in claim 11 in which said metal compound is applied by cathodic arc plasma deposition.

19. A process as in claim 18 wherein the stoichiometry of said metal compound may be altered in order to vary the color of said coat.

* * * * *

UNITED STATES PATENT AND TRADEMARK OFFICE
CERTIFICATE OF CORRECTION

PATENT NO. : 4,981,756

DATED : January 1, 1991

INVENTOR(S) : Randhawa

It is certified that error appears in the above-identified patent and that said Letters Patent is hereby corrected as shown below:

Column 6, line 33, "to" should read --by--.

Signed and Sealed this

Twelfth Day of May, 1992

Attest:

DOUGLAS B. COMER

*Attesting Officer*   *Acting Commissioner of Patents and Trademarks*